US012582764B2

(12) United States Patent
Limaye et al.

(10) Patent No.: US 12,582,764 B2
(45) Date of Patent: Mar. 24, 2026

(54) PEN NEEDLE MAGAZINE

(71) Applicant: Embecta Corp., Andover, MA (US)

(72) Inventors: Amit Limaye, Wayne, NJ (US); Dipumon Ayyanchira Mani, Kerala (IN); Praveesh Karattu Meethal, Kerala (IN); Sajayesh Vijayachandran, Kerala (IN)

(73) Assignee: Embecta Corp., Parsippany, NJ (US)

( * ) Notice: Subject to any disclaimer, the term of this patent is extended or adjusted under 35 U.S.C. 154(b) by 1126 days.

(21) Appl. No.: 17/615,452

(22) PCT Filed: Apr. 26, 2019

(86) PCT No.: PCT/US2019/029313
§ 371 (c)(1),
(2) Date: Nov. 30, 2021

(87) PCT Pub. No.: WO2020/219066
PCT Pub. Date: Oct. 29, 2020

(65) Prior Publication Data
US 2022/0226562 A1      Jul. 21, 2022

(51) Int. Cl.
*A61M 5/00*          (2006.01)
(52) U.S. Cl.
CPC ................................... *A61M 5/002* (2013.01)
(58) Field of Classification Search
CPC ....................................................... A61M 5/002
USPC ................................................. 206/366, 233
See application file for complete search history.

(56) References Cited

U.S. PATENT DOCUMENTS

| | | | |
|---|---|---|---|
| 5,971,966 A * | 10/1999 | Lav ..................... | A61M 5/3213 |
| | | | 604/110 |
| 8,887,912 B2 | 11/2014 | Chapin et al. | |
| 9,016,472 B2 | 4/2015 | Van Der Beek et al. | |
| 2001/0014792 A1 * | 8/2001 | West ..................... | A61M 5/002 |
| | | | 604/239 |
| 2002/0014430 A1 | 2/2002 | Groth | |
| 2002/0020647 A1 | 2/2002 | Groth | |
| 2003/0015444 A1 | 1/2003 | Molin et al. | |
| 2012/0041390 A1 | 2/2012 | Spool et al. | |
| 2015/0034516 A1 | 2/2015 | Chapin et al. | |
| 2019/0054231 A1 | 2/2019 | Spool et al. | |

FOREIGN PATENT DOCUMENTS

| | | | |
|---|---|---|---|
| EP | 2732835 A1 | 5/2014 | |
| JP | 2000271219 A | 10/2000 | |
| JP | 2012050820 A | 3/2012 | |
| JP | 2016501047 A | 1/2016 | |
| WO | 2017189909 A1 | 11/2017 | |

* cited by examiner

*Primary Examiner* — Jacob K Ackun
(74) *Attorney, Agent, or Firm* — Greenberg Traurig, LLP; Roman Fayerberg; David J. Dykeman

(57)          ABSTRACT

A pen needle magazine (10) comprising a plurality of compartments (14) each carrying a pen needle (40), and a pen needle carrier (60) disposed in each of the plurality of compartments (14), the pen needle (40) disposed in the pen needle carrier (60), wherein the pen needle carrier (60) includes a first pen needle path (62) and a second pen needle path (64), the first pen needle path (62) aids in removing the pen needle (40), and the second pen needle path (64) aids in discarding a used pen needle (40).

20 Claims, 19 Drawing Sheets

PEN NEEDLE MAGAZINE

FIELD OF THE INVENTION

Various exemplary embodiments of the invention relate to pen needle storage and disposal for medication delivery pens.

BACKGROUND OF THE INVENTION

Medication pens are typically used to inject medication into a patient. A person who must periodically self-inject doses of medication will typically carry a medication pen, several single-use pen needles, and several cleaning swabs. A medication pen is designed for safety and sterility. However, inefficiencies and inconveniences can arise.

SUMMARY OF THE INVENTION

It is an aspect of the present invention to provide a pen needle magazine that stores a plurality of needles configured to engage a medication pen for medication delivery. Such a magazine provides advantages in easy organization, allows for needle disposal after use and storage before use in the same magazine and improves usage with an optimized workflow to reduce setup time and space. Needle disposal after use and storage before use allows for synchronized pen needle attachment and removal, as well as pen needle detachment and disposal. Finally, the controlled movement of the pen needle attachment and removal from the magazine reduces user needle sticking and reduces accidental bending of a needle in the pen needle.

The pen needle magazine also reduces the likelihood of pen needle reuse in several ways. First, the pen needle magazine has a seal tab that acts as a visual indicator to indicate to a user whether the pen needle is used or new. Second, a first position of the unused pen needle is disposed near the top surface of the pen needle magazine. After the pen needle is used and subsequently discarded into the pen needle magazine, the pen needle is disposed in a second position deeper into a compartment of the pen needle magazine. This second position prevents a non-patient end of the pen needle from exposure and access after disposal, which reduces the opportunity of a needle stick. Finally, in the second position, the pen needle is locked into the compartment of the pen needle magazine to provide positive feedback of needle disposal.

The foregoing and/or other aspects of the present invention can be achieved by providing a pen needle magazine comprising a plurality of compartments each carrying a pen needle, a seal disposed on a top surface of each of the plurality of compartments to enclose each of the pen needles in a corresponding compartment, and a plurality of compartment doors that each cover the corresponding compartment, wherein each seal is disposed between the top surface of one of the plurality of compartments and a corresponding compartment door.

The foregoing and/or other aspects of the present invention can further be achieved by providing a pen needle magazine comprising a plurality of compartments each carrying a pen needle, and a pen needle orientate (pen needle carrier) disposed in each of the plurality of compartments, the pen needle disposed in the pen needle orientate, wherein the pen needle orientate includes a first pen needle path and a second pen needle path, the first pen needle path aids in removing the pen needle, and the second pen needle path aids in discarding a used pen needle.

The foregoing and/or other aspects of the present invention can also be achieved by providing a method of using a plurality of pen needles stored in a housing, the method comprising connecting a unused pen needle to a medication delivery pen for medication delivery; removing the unused pen needle from a first position in a cavity of the housing; administering medication via the pen needle connected to the medication delivery pen; disposing of the used pen needle, after medication delivery, in a second position in the cavity of the housing; and sending the housing to a manufacturer or a waste management entity after use of all of the plurality of pen needles in the housing.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which.

DETAILED DESCRIPTION OF EXEMPLARY EMBODIMENTS

Figure 1:
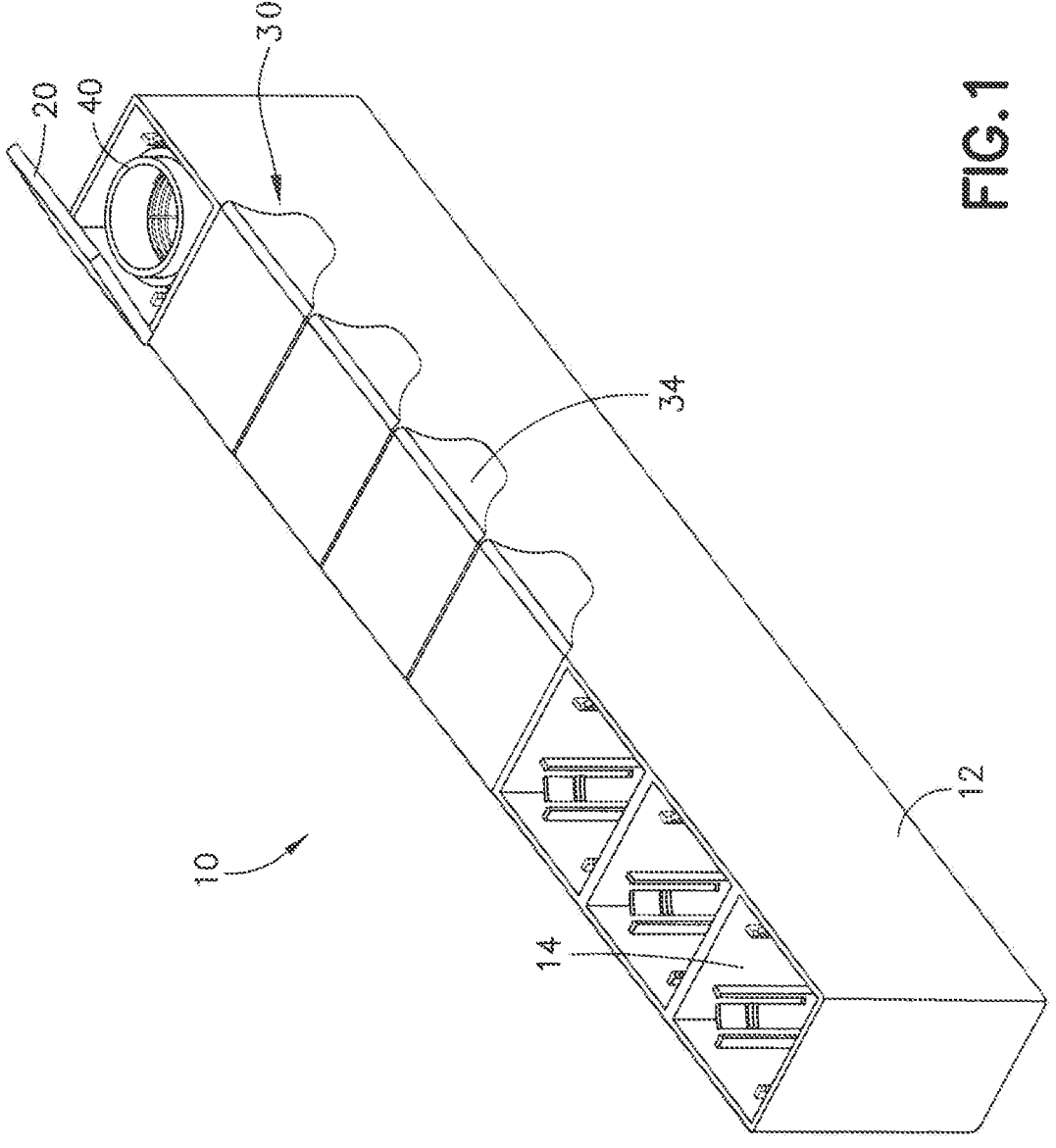
FIG. 1 shows a perspective view of an exemplary pen needle magazine.

According to one embodiment, FIG. 1 illustrates a pen needle magazine 10 configured to carry a plurality of pen needles 40. The pen needle magazine 10 includes a magazine housing 12, a plurality of compartments 14 and a plurality of compartment doors 20. The magazine housing 12 is a substantially rectangular shaped linear array of adjacent compartments 14. Each of the plurality of compartments 14 is substantially square shaped and includes a cavity to carry a pen needle 40. Each of the plurality of compartment doors 20 is hinged on one side of the magazine housing 12 and is configured to open and close to cover and provide access to a corresponding compartment 14 of the plurality of compartments 14. Such a configuration advantageously provides an easy organization of pen needles 40.

Figure 20:
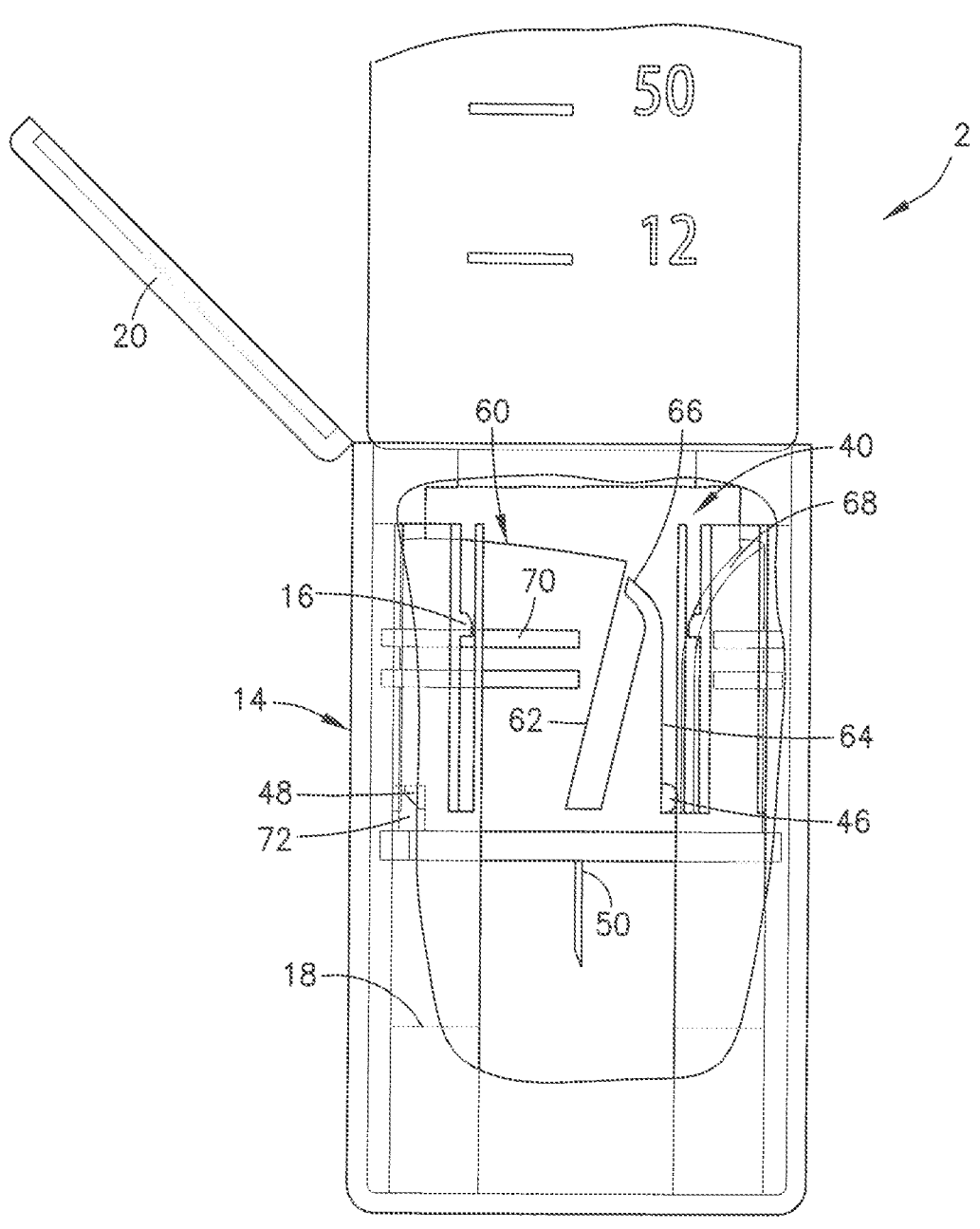
FIG. 20 shows the pen needle engaged to the pen needle orientate in the compartment of FIG. 19 moving toward the second position.
Figure 21:
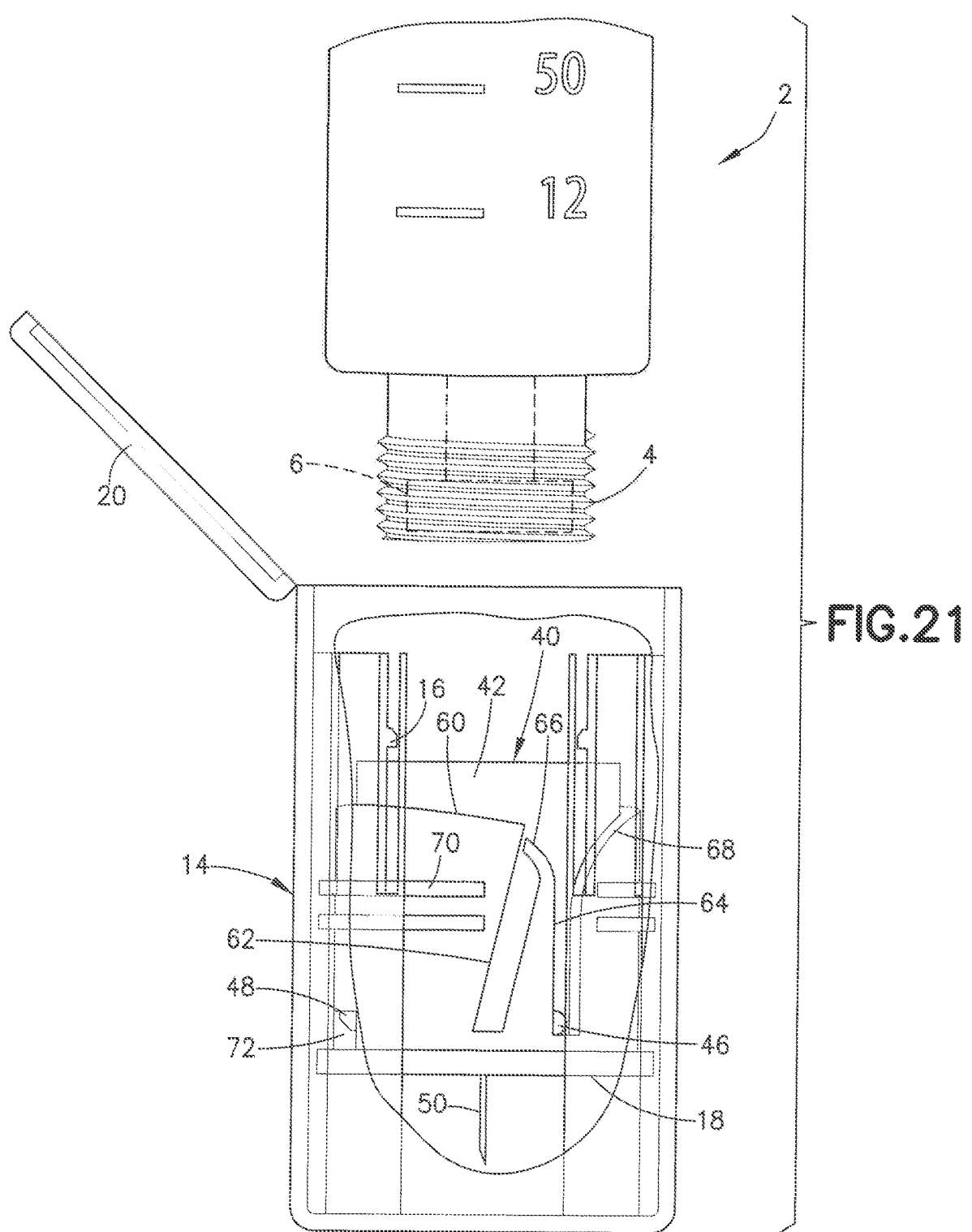
FIG. 21 shows the pen needle engaged to the pen needle orientate in the compartment of FIG. 20 in the second position.

The plurality of compartments 14 further includes a compartment-retaining element 16 and a bottom-stepped surface 18 as more clearly shown in FIGS. 20 and 21, for example. The compartment-retaining element 16 includes a chamfered flange that advantageously allows for downward movement of a pen needle orientate 60, also known as a pen needle carrier 60. Specifically, a top surface of the compartment-retaining element 16 is chamfered to allow for smooth movement of the pen needle orientate 60 in the compartment 14.

A bottom surface of the compartment-retaining element 16 is a flat surface. Accordingly, the pen needle orientate 60 is not able to move upward beyond the flat bottom surface of the compartment-retaining element 16. As a result, the pen needle orientate 60 is locked within the compartment 14. The pen needle orientate 60 can advantageously be inserted in the compartment 14 but cannot be removed. Further details of the interaction between the compartment 14 and pen needle orientate 60 are described below.

Figure 2:
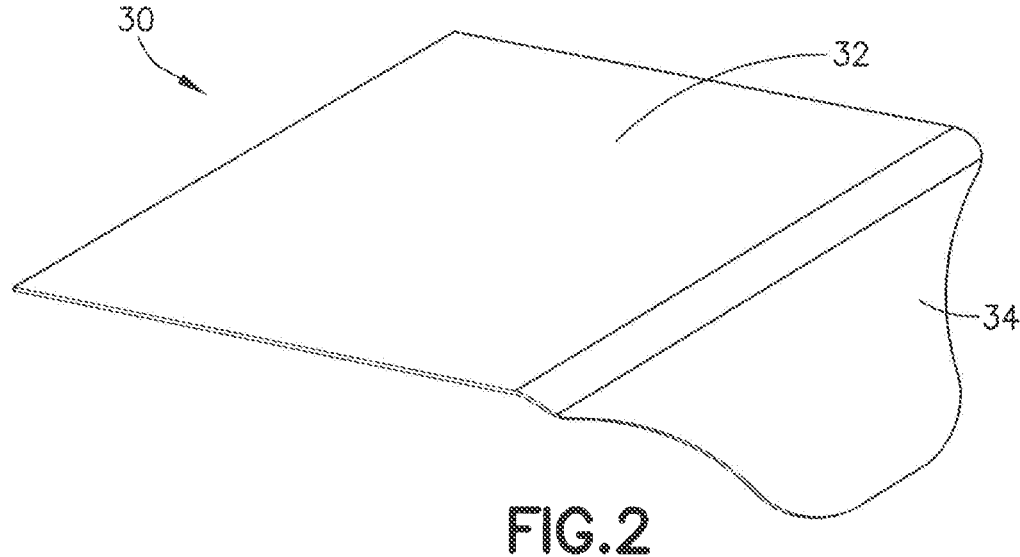
FIG. 2 shows a perspective view of a seal configured to be connected to the pen needle magazine of FIG. 1.

Before the pen needles 40 are accessed from the plurality of compartments 14, each of the plurality of compartments 14 is enclosed by a seal 30. FIG. 1 illustrates a plurality of seals 30 each enclosing one of the plurality of compartments 14. Although seals 30 are shown on only some of the compartments 14, all of the compartments 14 would typically have seals 30 prior to use. FIG. 2 illustrates the seal 30 in more detail.

Specifically, the seal 30 includes a sealing portion 32 and a tab portion 34. The sealing portion 32 is disposed directly above a top surface of the respective compartment 14 to enclose the pen needle 40 in the compartment 14. When the compartment door 20 is secured to the magazine housing 12, the compartment door 20 covers the sealing portion 32 to advantageously prevent accidental puncturing. Thus, the sealing portion 32 is sandwiched between the top surface of the compartment 14 and the compartment door 20 in the closed position of the compartment 14.

On the other hand, the tab portion 34 is adjacent to the corresponding compartment 14. The tab portion 34 is not disposed between the compartment door 20 and the compartment 14. Thus, the user is able to access and use the tab portion 34 to open the compartment door 20. Specifically, the user holds the tab portion 34 and pulls upward to open the compartment door 20 and remove the sealing portion 32 from the top surface of the compartment 14. The tab portion 34 also acts as a visual indicator for the user outside of the closed compartment door 20 to indicate that the pen needle 40 is enclosed in the compartment 14 by the seal 30. Accordingly, such a configuration advantageously indicates that the pen needle 40 is unused and ready for use.

Figure 3:
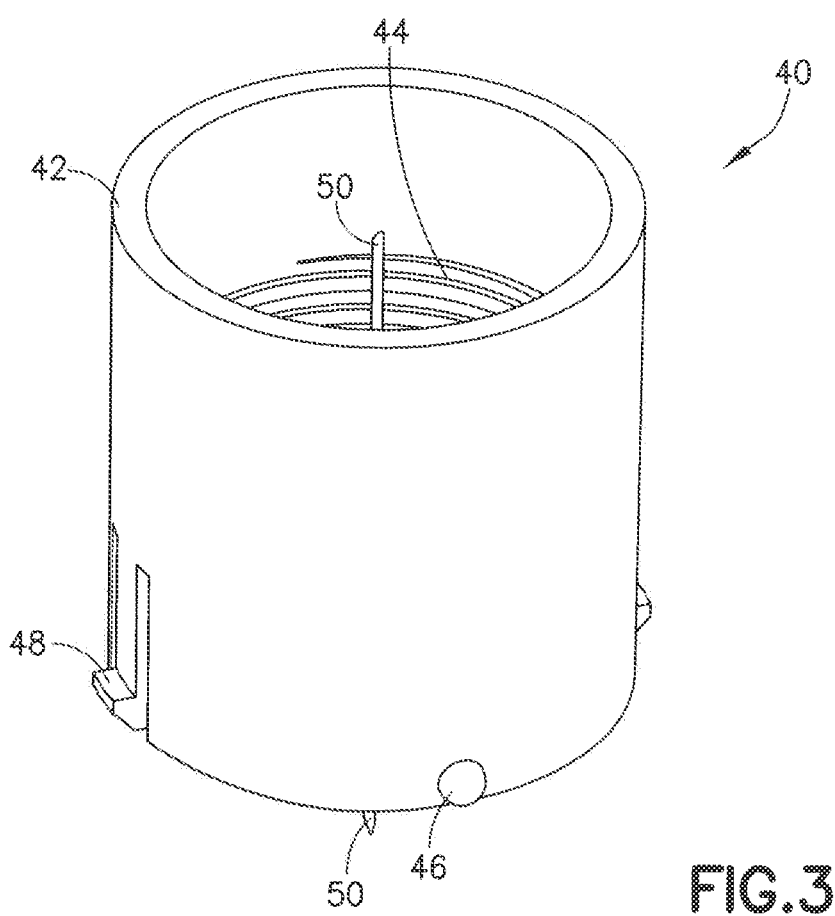
FIG. 3 shows a perspective view of a pen needle configured to be disposed in the pen needle magazine of FIG. 1.

FIG. 3 illustrates the pen needle 40. The pen needle 40 includes a hub 42, an inner thread 44, a follower guide element 46, a pen needle snap lock 48 and a needle 50. The hub 42 is the housing or base of the pen needle 40. The inner thread 44 is configured to attach to an outer thread 4 of a medication delivery pen 2 (see FIG. 11). Upon full engagement of the inner thread 44 to the outer thread 4, a non-patient end of the needle 50 pierces a septum 6 of the medication delivery pen 2 to establish fluid communication.

The follower guide element 46 is a substantially dome-shaped protrusion disposed on an external circumferential surface of the pen needle 40 and at a distal end of the pen needle 40. As described below, the follower guide element 46 advantageously guides the pen needle 40 into engagement and disengagement with the pen needle orientate 60 (see FIG. 4). Preferably, two follower guide elements 46 are substantially positioned 180° apart from each other on the circumferential, distal surface of the pen needle 40.

The pen needle 40 further includes a pen needle snap lock 48. The pen needle snap lock 48 is also disposed on an external circumferential surface of the pen needle 40 and at a distal end of the pen needle 40. The pen needle snap lock 48 is a cantilevered tab (see FIG. 16) that flexes inwardly (disengaged) and expands outwardly (engage) in a resting position to engage and disengage the pen needle orientate 60. The pen needle snap lock 48 is angularly positioned with respect to the follower guide element 46. As further described below, this angular arrangement allows the pen needle 40 to lock to the pen needle orientate 60 after use of the pen needle 40.

Finally, the pen needle 40 includes the needle 50 as conventionally understood by one of ordinary skill in the art. During use, the needle 50, specifically a patient end of the needle 50, provides fluid communication between the medication delivery pen 2 and the patient. In addition, when the pen needle 40 is attached to the outer thread 4 of the medication delivery pen 2, a proximal end of the needle 50 pierces the septum 6 of the medication delivery pen 2 to establish fluid communication.

Figure 4:
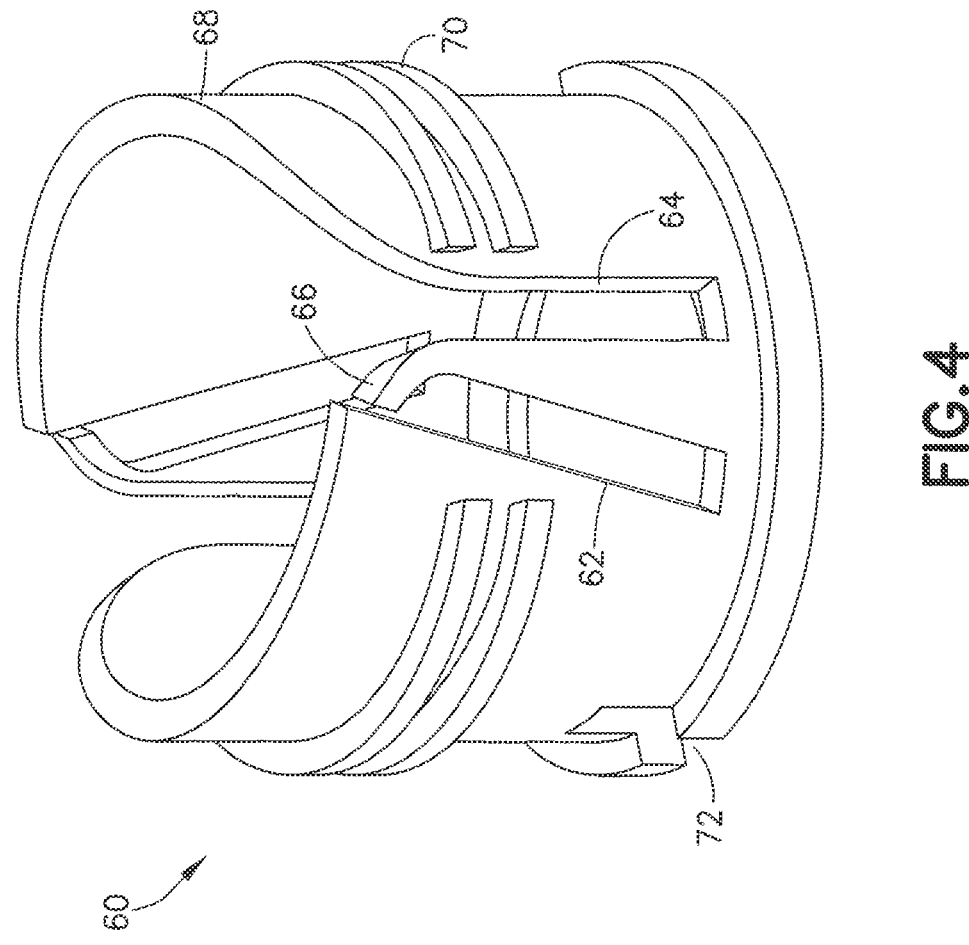
FIG. 4 shows a perspective view of a pen needle orientate configured to be disposed in the pen needle magazine of FIG. 1.

FIG. 4 illustrates the pen needle orientate 60. The pen needle orientate 60 is a pen needle carrier that aids in orienting and supporting the pen needle 40 for removal out of the compartment 14 and placement into the compartment 14 of the magazine housing 12. The pen needle orientate 60 is a movable hollow member having an opening extending through a proximal and distal end. The pen needle orientate 60 includes a first pen needle path 62, a second pen needle path 64, a path obstruction 66, a pen needle path curvature 68, a pen needle orientate retaining element 70 and a pen needle orientate snap lock 72. Each of these features is described below.

The first pen needle path 62 is a slot disposed through an outer circumferential surface of the pen needle orientate 60 and into the opening. That is, the first pen needle path 62 also extends through the outer surface of the pen needle orientate 60. The slot of the first needle path 62 is angled upward at an angle between approximately 15°-30°, for example, with respect to the rotational axis. The pen needle orientate 60 preferably includes two first pen needle paths 62 positioned at substantially 180° apart from each other with respect to the rotational axis of the pen needle orientate 60.

The first pen needle path 62 is exclusively used to guide a new, unused pen needle 40. Specifically, when the unused pen needle 40 is disposed in the pen needle orientate 60, the follower guide element 46 of the pen needle 40 is positioned within the first pen needle path 62. As the user removes the pen needle 40, the follower guide element 46 slides up the first pen needle path 62 and the pen needle orientate 60 rotates in a controlled manner to disengage the pen needle 40 from the pen needle orientate 60. This controlled guiding advantageously prevents accidental bending of the needle 50 in the pen needle 40. The operational relationship between the pen needle 40 and the pen needle orientate 60 is further described below.

The second pen needle path 64 is a substantially vertical slot adjacent to the first pen needle path 62 and parallel to the rotational axis. Similar to the first pen needle path 62, the second pen needle path 64 extends through the outer surface of the pen needle orientate 60. The pen needle orientate 60 also preferably includes two second pen needle paths 64 positioned substantially 180° apart with respect to the rotational axis of the pen needle orientate 60.

Figure 7:
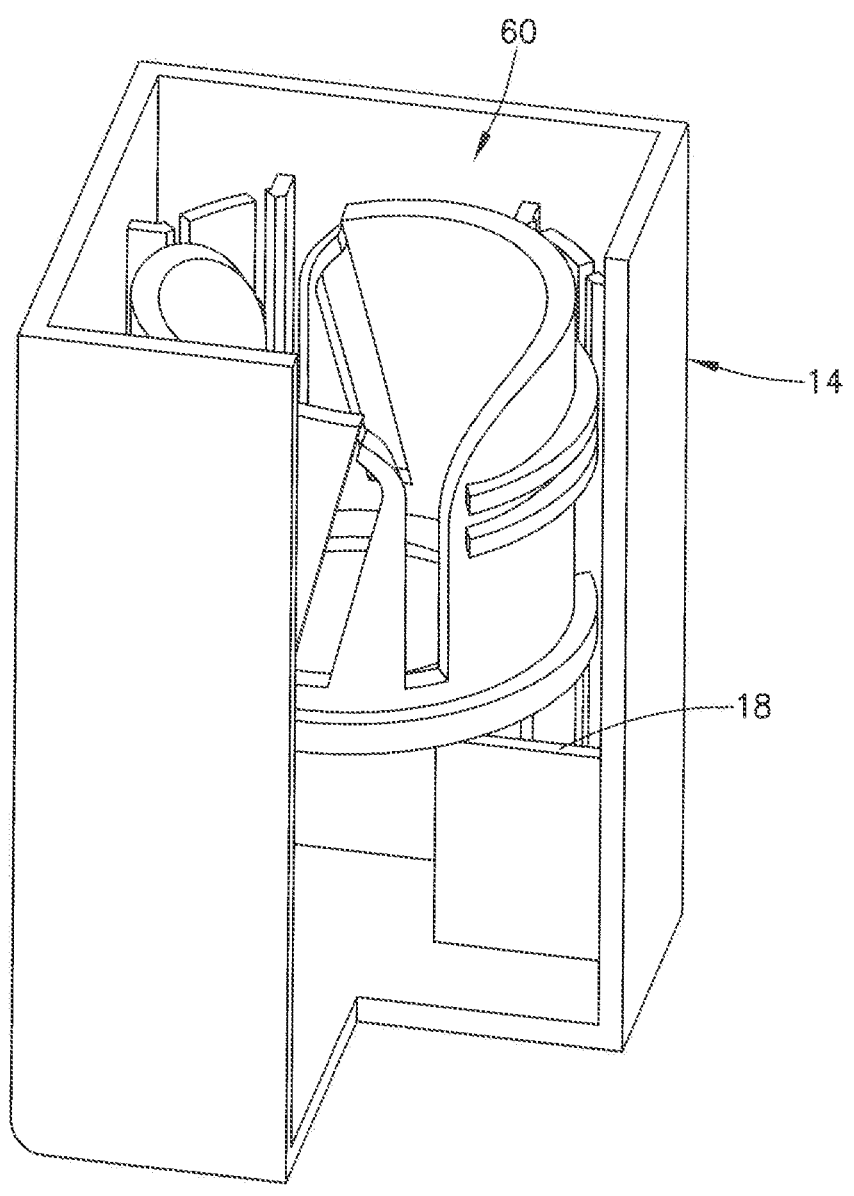
FIG. 7 shows a perspective view of a pen needle orientate disposed in the compartment of FIG. 6.

The pen needle path curvature 68, as illustrated in FIG. 4, is a downwardly curved surface on a proximal end of the pen needle orientate 60. Specifically, each of a proximal end of the second pen needle paths 64 is disposed at the end of the pen needle path curvature 68. Accordingly, the second pen needle path 64 in cooperation with the pen needle path curvature 68 is exclusively used to guide a used pen needle 40 into the pen needle orientate 60. When the used pen needle 40 begins to engage the pen needle orientate 60, the follower guide element 46 travels on the pen needle path curvature 68. As illustrated in FIG. 7, the pen needle path curvature 68 guides the follower guide element 46 into the second pen needle path 64. Subsequently, the follower guide element 46 travels downward to the distal end of the second pen needle path 64. This controlled guiding advantageously prevents accidental bending of the needle 50 in the pen needle 40.

The pen needle orientate 60 also includes a path obstruction 66. The path obstruction 66 includes a thin, curved inner and outer surface on one side of the slot of the first pen needle path 62 for flexibility and guiding purposes. The path obstruction 66 is disposed at a proximal end of the first pen needle path 62 and advantageously acts as a one-way valve. Specifically, as the pen needle 40 is moved upward in the pen needle orientate 60, the thin, curved inner surface of the path obstruction 66 guides the follower guide element 46 of the new pen needle 40 to exit the first pen needle path 62. When the follower guide element 46 contacts the path obstruction 66 to exit the first pen needle path 62, the path obstruction 66 selectively opens by elastically deflecting outward (valve opens) so that the first pen needle path 62 is unobstructed. The follower guide element 46 can then exit the first pen needle path 62.

On the other hand, when the used pen needle 40 engages the pen needle orientate 60, the curved outer surface of the path obstruction 66 directs the follower guide element 46 toward the second pen needle path 64, as illustrated in FIG. 7. The path obstruction 66 does not deflect outwardly (valve closed). Thus, the follower guide element 46 of the used pen needle 40 can only engage the second pen needle path 64 and not the first pen needle path 62 to return the pen needle 40 inside of the pen needle orientate 60.

As illustrated in FIG. 4, the pen needle orientate 60 also includes a pen needle orientate retaining element 70. The pen needle orientate retaining element 70 is a protruded surface with a groove centrally disposed on the protruded surface and in a circumferential direction. The pen needle orientate retaining element 70 extends circumferentially along an outer surface of the pen needle orientate 60 and does not interfere with the first and second pen needle paths 62, 64. The pen needle orientate retaining element 70 interacts with the compartment-retaining element 16 to engage and disengage as described above. Specifically, this interaction allows the pen needle orientate 60 to move from a first position (top position) to a second position (bottom position) and an audible sound or tactile feedback is provided to indicate such movement. This interaction also allows the pen needle orientate 60 to rotate in the first position of the compartment 14. Further operation of this interaction is described below.

Finally, the pen needle orientate 60 includes a pen needle orientate snap lock 72 that locks the pen needle 40 to the pen needle orientate 60. The pen needle orientate snap lock 72 is an opening disposed on a distal end of the pen needle orientate 60 that is configured to engage the pen needle snap lock 48. The second pen needle path 64 is angularly positioned with respect to the pen needle orientate snap lock 72. In this manner, the pen needle 40 is advantageously locked to the pen needle orientate 60 only when the follower guide element 46 travels to the distal end of the second pen needle path 64. When the pen needle 40 is disposed in the distal end of the second pen needle path 64, the pen needle snap lock 48 expands to engage and lock to the pen needle orientate snap lock 72.

The pen needle orientate snap lock 72 does not engage the pen needle snap lock 48 when the follower guide element 46 is in the first pen needle path 62. Instead, the pen needle snap lock 48 is flexed inwardly in the opening of the pen needle orientate 60 and misaligned from the pen needle orientate snap lock 72.

Figure 5:
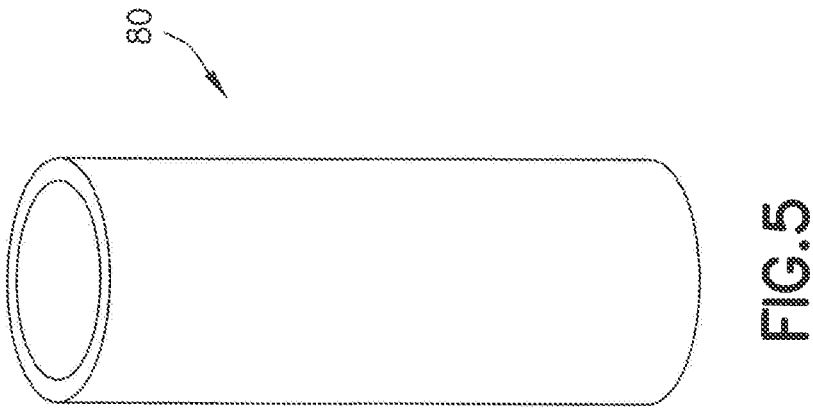
FIG. 5 shows a perspective view of an inner shield configured to cover a needle of the pen needle of FIG. 3.

FIG. 5 illustrates an inner shield 80. The inner shield 80 includes an open proximal end, a closed distal end and a cavity therebetween. The inner shield 80 is used to cover the needle 50 of the pen needle 40 prior to use to prevent the needle 50 from bending and to avoid accidental needle sticking. The inner shield 80 also ensures that the pen needle orientate 60 stays in the first position and does not enter into and lock in the second position.

Figure 6:
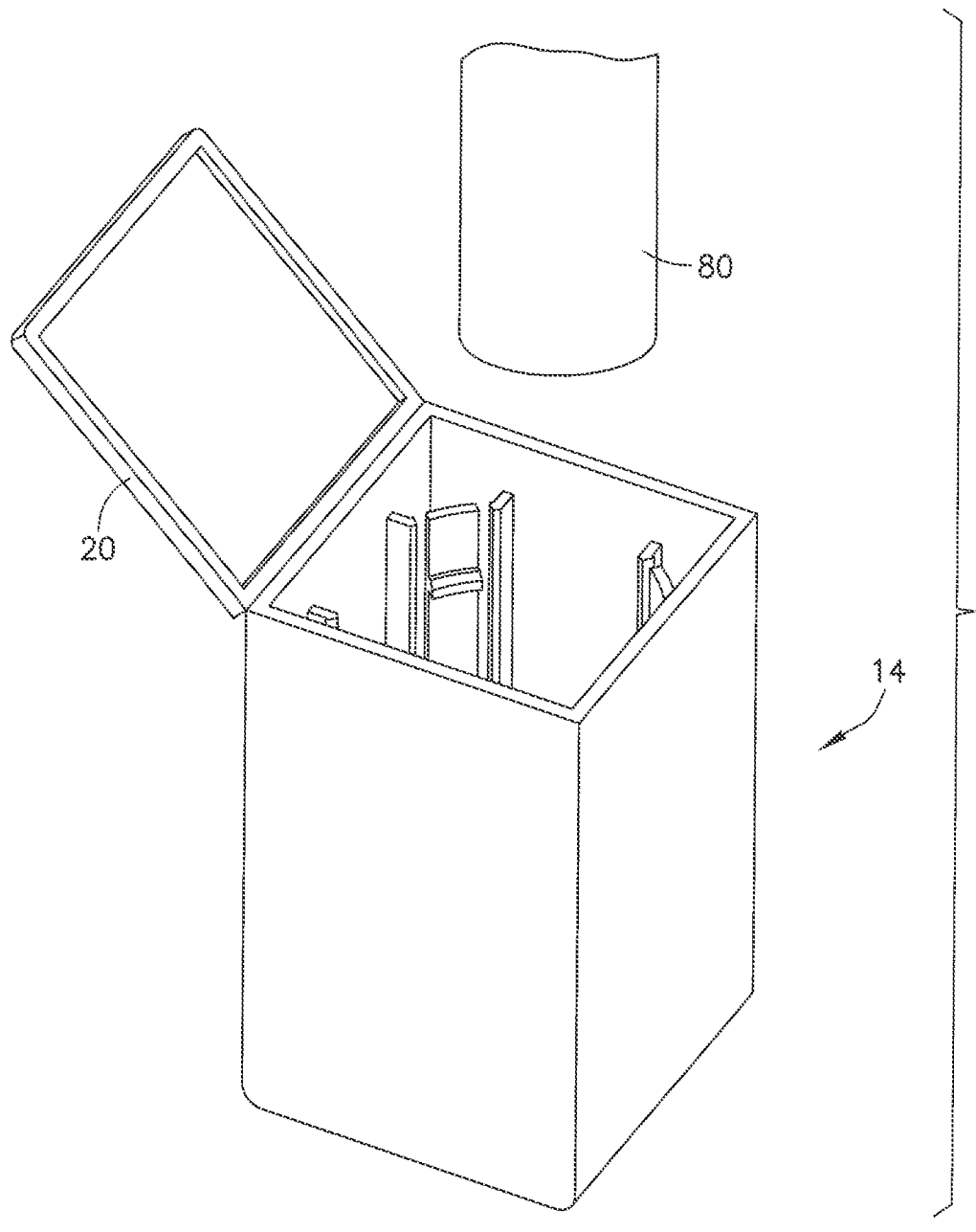
FIG. 6 shows a perspective view of a compartment of the pen needle magazine of FIG. 1.

After the pen needle 40 is removed from the compartment 14, as illustrated in FIG. 6, the inner shield 80 is removed and discarded. When the pen needle 40 is returned to the compartment 14 after use, the inner shield 80 is no longer used. Instead, the pen needle orientate 60 is now able to move to the second position and contact the bottom-stepped surface 18 as illustrated in FIGS. 7 and 21, for example.

Figure 8:
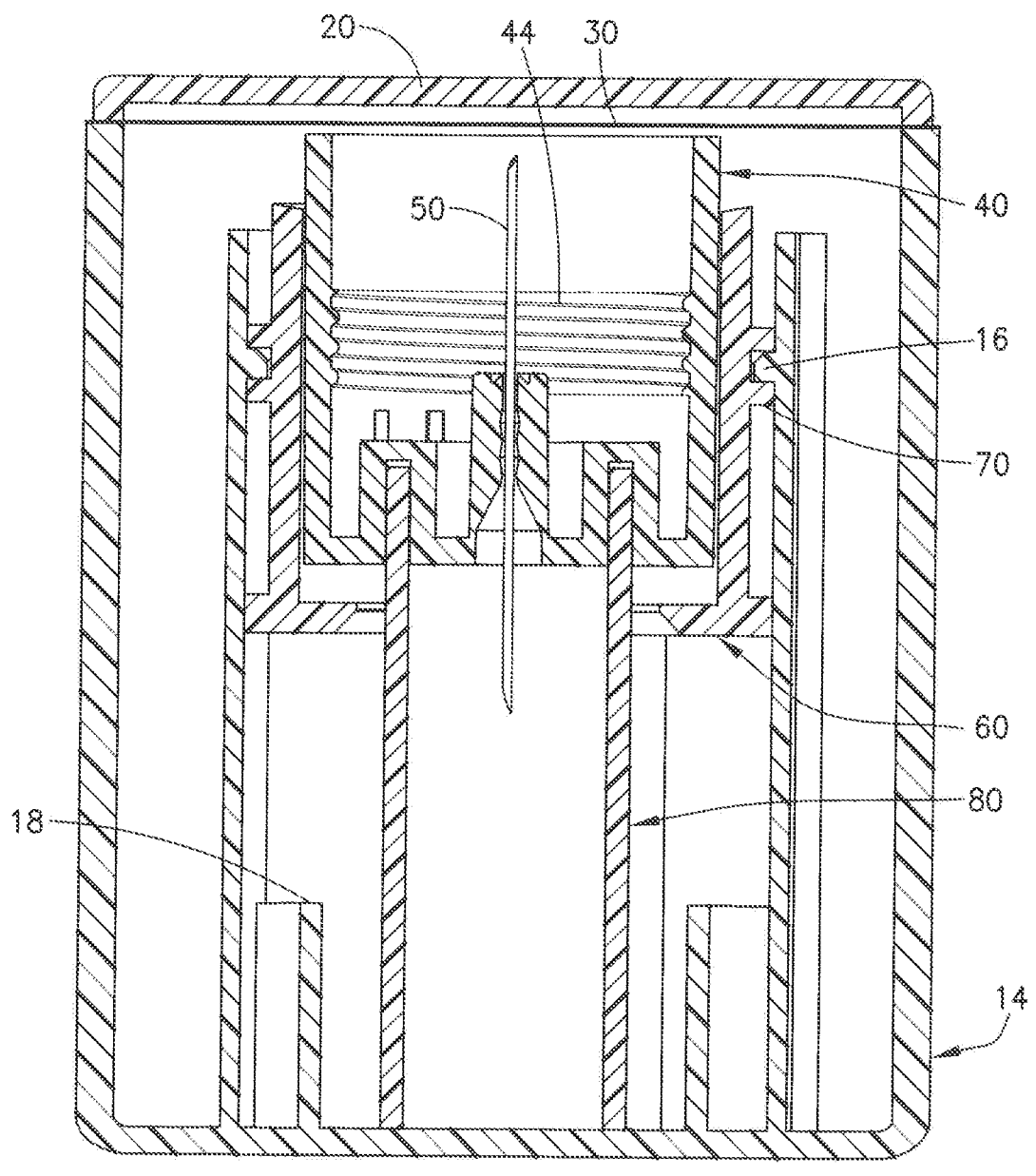
FIG. 8 shows a cross-sectional view of the compartment in the pen needle magazine of FIG. 1 in a closed position.

Detailed operation of the pen needle magazine 10 is described as follows. FIG. 8 illustrates one of the plurality of compartments 14 in a closed position. In this position, the compartment 14 is enclosed by the seal 30 and the compartment door 20 is advantageously disposed over the seal 30 to further cover the compartment 14 and protect the seal 30 from inadvertent puncture.

Figure 9:
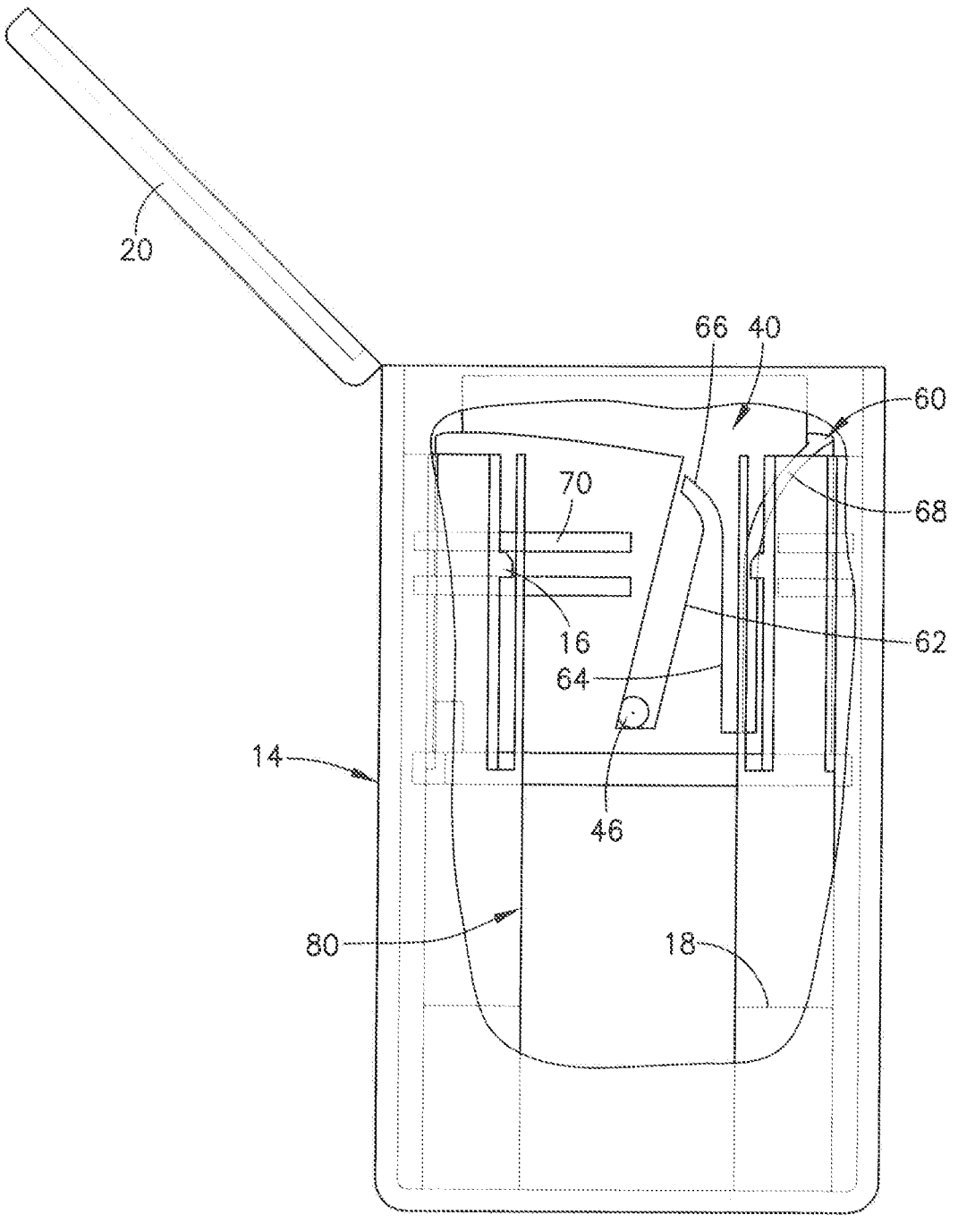
FIG. 9 shows a cross-sectional view of the compartment of FIG. 8 in an open position and the pen needle in a first position.
Figure 10:
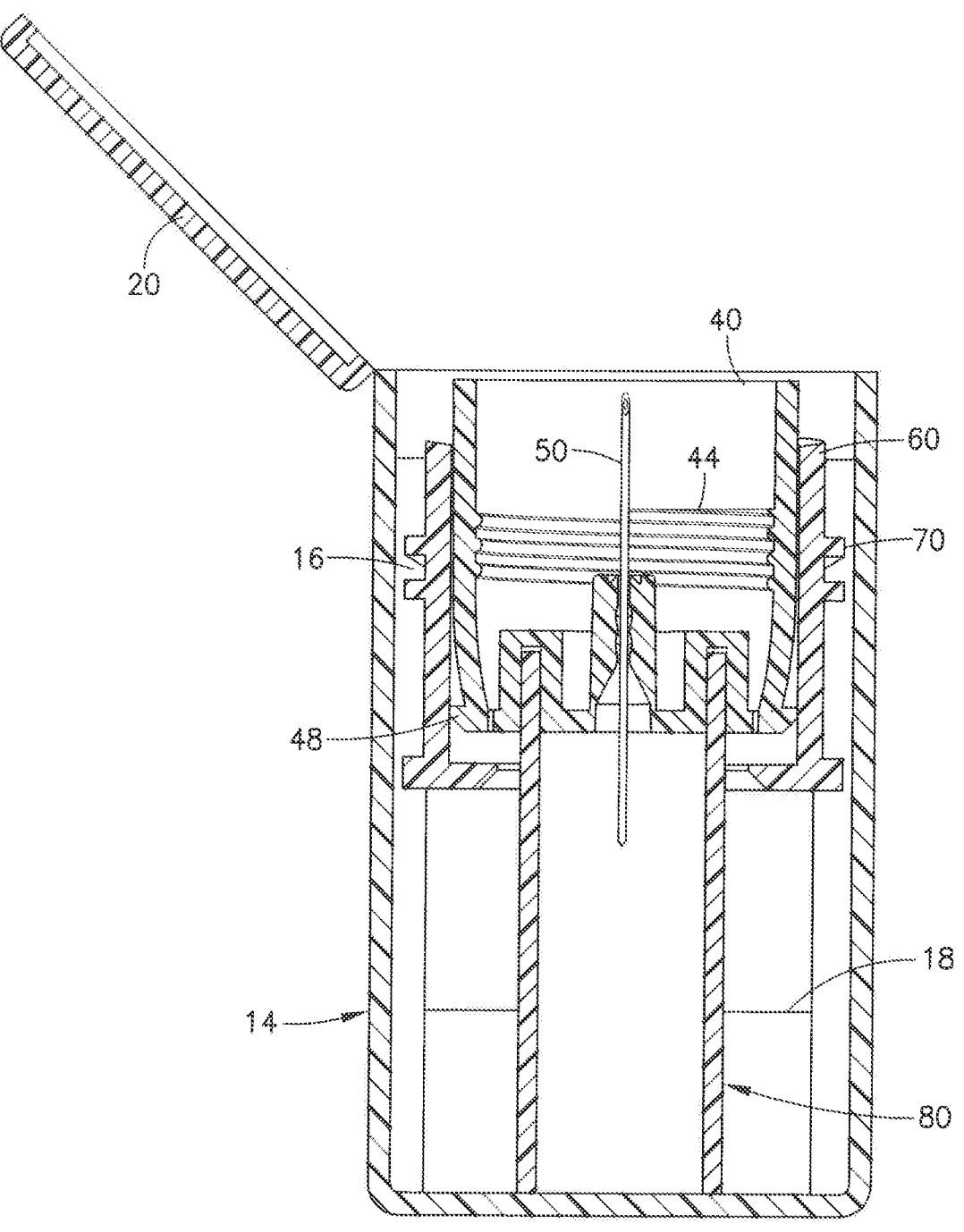
FIG. 10 shows an alternate cross-sectional view of the compartment of FIG. 8 in an open position and the pen needle in a first position.

The pen needle orientate 60 is locked in the compartment 14 at the first position for the user to access the pen needle 40 disposed in the pen needle orientate 60. Specifically, FIGS. 8-10 show that the first position is characterized by the pen needle orientate retaining element 70 engaging the compartment-retaining element 16. The inner shield 80 covers the needle 50 to protect the distal tip. The use of the inner shield 80 also prevents the pen needle orientate 60 from traveling further downward into the compartment 14.

FIG. 9 illustrates an open position of the compartment door 20 where the tab portion 34 of the seal 30 is pulled by the user to remove the sealing portion 32 from the top surface of the compartment 14. At the same time, the compartment door 20 is also opened. The pen needle orientate 60 is disposed in the first position where the pen needle 40 is ready for removal and use. The follower guide element 46 is disposed at a distal end of the first pen needle path 62 of the pen needle orientate 60 which also indicates that the pen needle 40 is ready for removal and use. The first position is visible to the user and advantageously acts as a visual indicator that the pen needle 40 is ready for operation.

FIG. 10 shows an alternate view of the configuration illustrated in FIG. 9. Specifically, FIG. 10 shows that the pen needle snap lock 48 is flexed inwardly on an inner diameter of the opening of the pen needle orientate 60. In other words, the pen needle 40 is not locked to the pen needle orientate 60 and is ready for removal and use.

Figure 11:
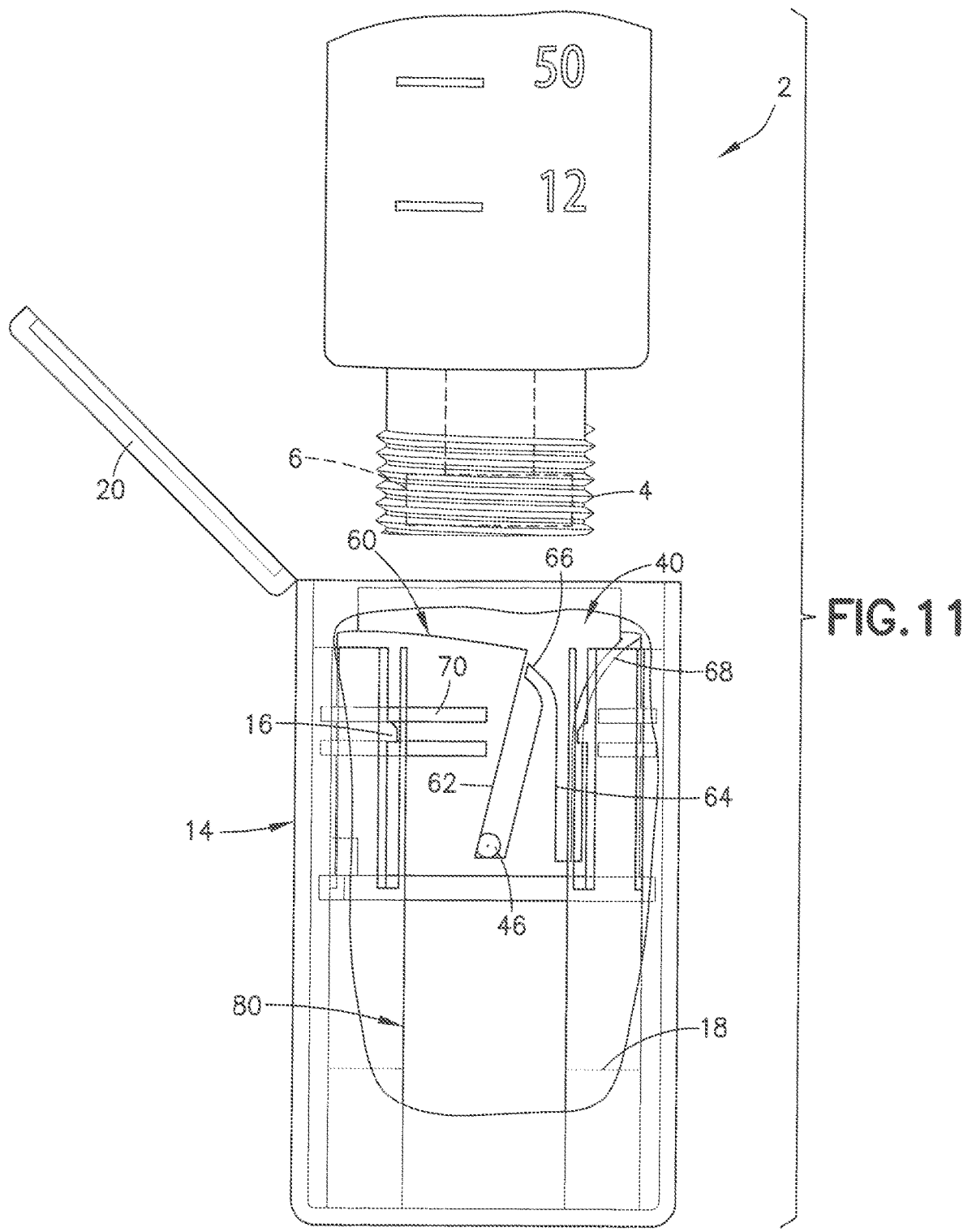
FIG. 11 shows a medication delivery pen preparing to engage the compartment of FIG. 9.

FIG. 11 illustrates the medication delivery pen 2 prior to engaging the pen needle 40. The pen needle 40 is in the first position as described above with respect to FIGS. 8-10. Specifically, the compartment-retaining element 16 of the compartment 14 is engaged to the pen needle orientate retaining element 70 of the pen needle orientate 60.

Figure 12:
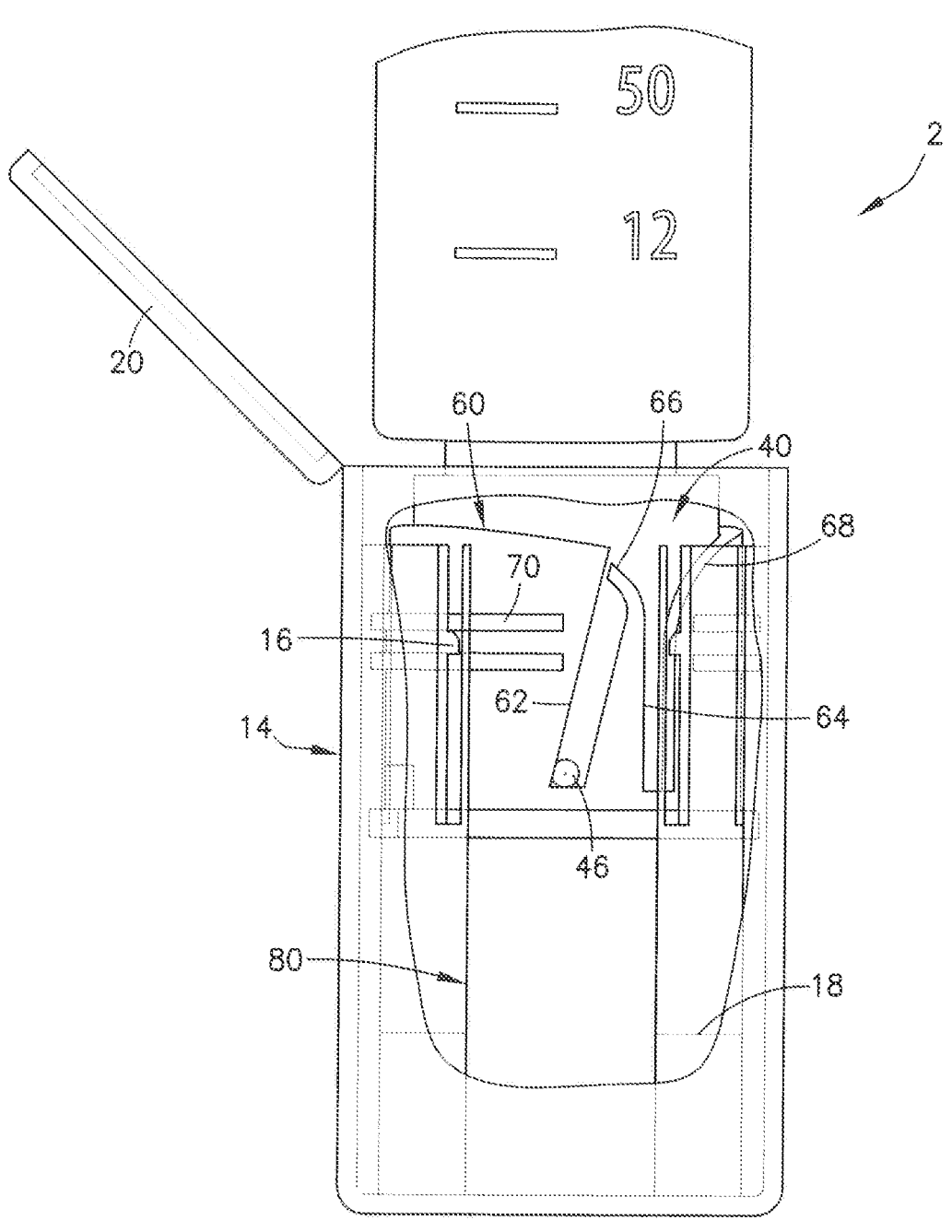
FIG. 12 shows the medication delivery pen engaged to the pen needle in the compartment of FIG. 9.

FIG. 12 illustrates the medication delivery pen 2 engaged to the pen needle 40. Specifically, the external thread 4 on the medication delivery pen 2 threads into and engages the inner thread 44 of the pen needle 40. When the medication delivery pen 2 fully engages the pen needle 40, the proximal end of the needle 50 (non-patient end) pierces the septum 6 and provides fluid communication between the distal end (patient end) of the pen needle 40 and the medication delivery pen 2.

Figure 13:
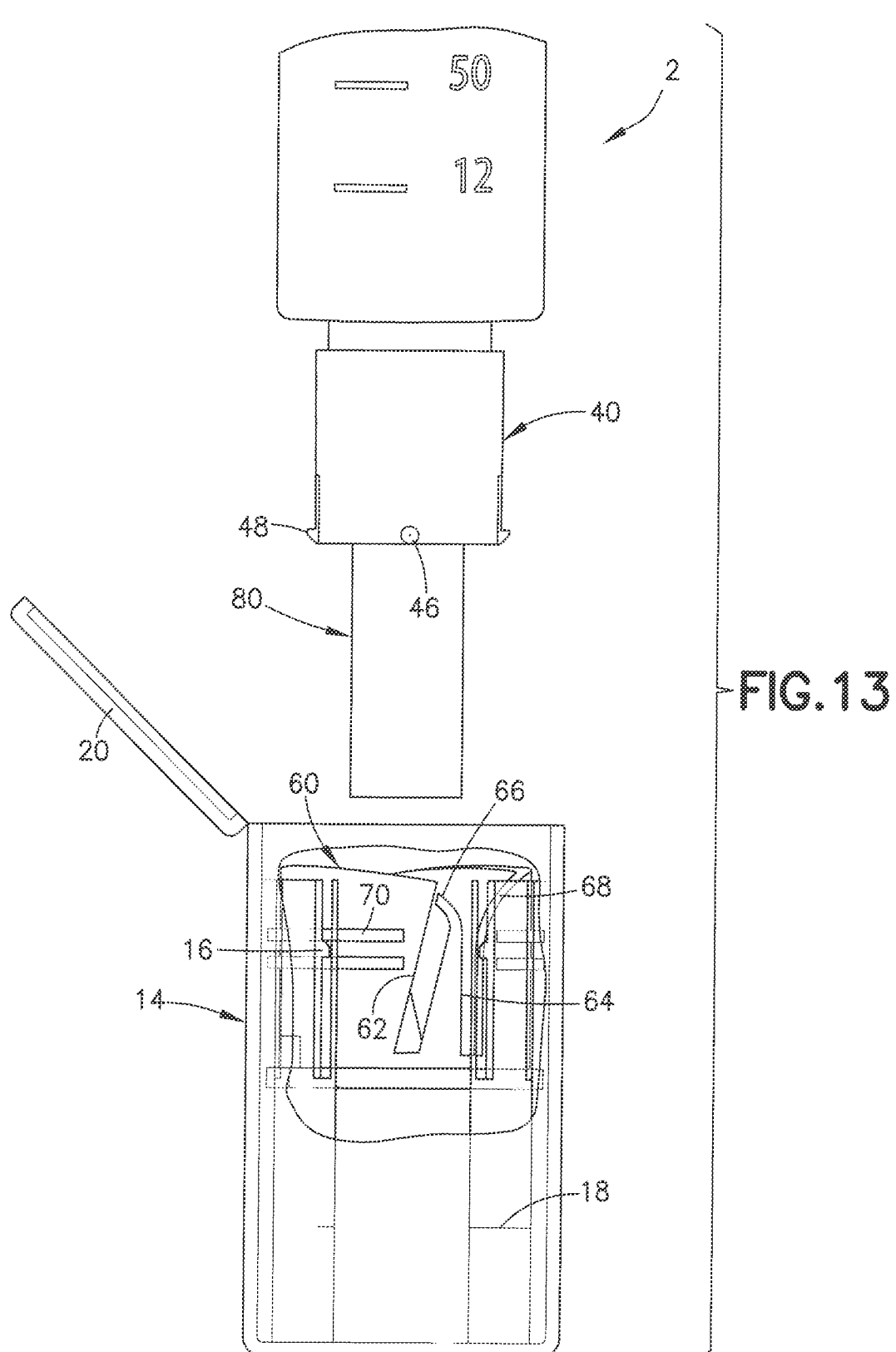
FIG. 13 shows removal of the medication delivery pen, pen needle and an inner shield from the compartment of FIG. 12.

FIG. 13 illustrates the user moving the medication delivery pen 2 upward to remove the attached pen needle 40. As the pen needle 40 is removed from the compartment 14, the follower guide element 46 of the pen needle 40 travels upward and is guided within the first pen needle path 62 of the pen needle orientate 60. The pen needle orientate 60 simultaneously rotates in a clockwise direction in the first position to provide easy and smooth removal of the pen needle 40.

Figure 14:
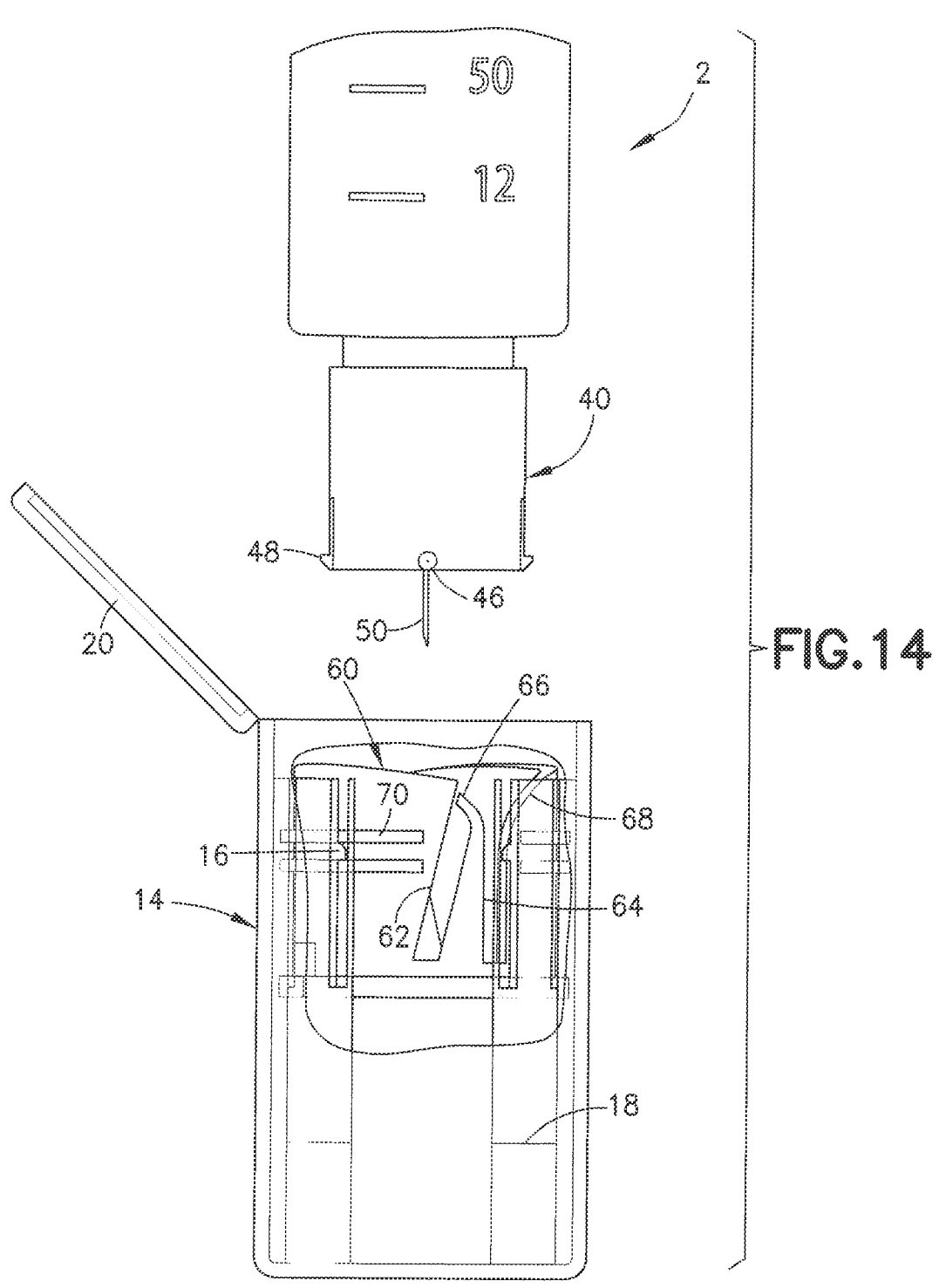
FIG. 14 shows removal of the inner shield from the pen needle attached to the medication delivery pen of FIG. 13.

As the follower guide element 46 travels upward and contacts the path obstruction 66 of the pen needle orientate 60, the follower guide element 46 causes the path obstruction 66 to elastically deflect outward. This advantageously allows the follower guide element 46 to exit the first pen needle path 62. The inner shield 80 is also removed from the compartment 14 and covers the distal end of the needle 50 (patient end) in the pen needle 40. FIG. 14 illustrates the pen needle 40 attached to the medication delivery pen 2 with the inner shield 80 removed. The medication delivery pen 2 is now ready for injection and administration of medicament.

Figure 15:
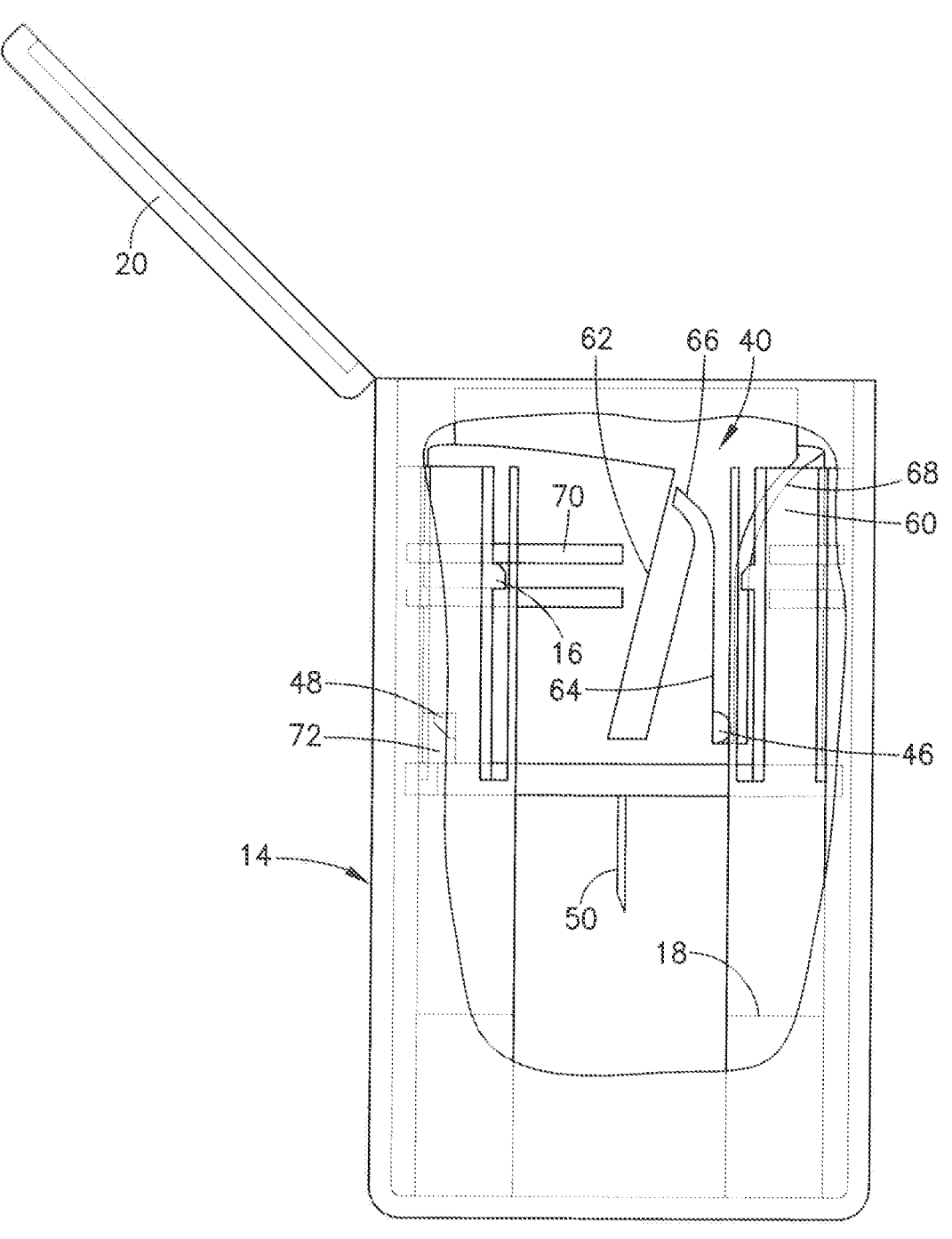
FIG. 15 shows a cross-sectional view of the compartment in the pen needle magazine of FIG. 1 with the used pen needle returned to the first position.

FIG. 15 shows the pen needle 40 after use and disposed at the first position of the compartment 14. However, in this first position, the follower guide element 46 of the pen needle 40 is disposed in the second pen needle path 64 of the pen needle orientate 60. Specifically, the pen needle path curvature 68 and/or the curved outer surface of the path obstruction 66 of the pen needle orientate 60 advantageously guides the follower guide element 46 into the second pen needle path 64. This controlled guiding advantageously prevents accidental bending of the needle 50 in the pen needle 40. The follower guide element 46 does not enter into the first pen needle path 62 because of the path obstruction

66. Accordingly, the path obstruction 66 advantageously acts like a one-way valve and can only be opened when the follower guide element 46 exits the first pen needle path 62 as described above.

Figure 16:
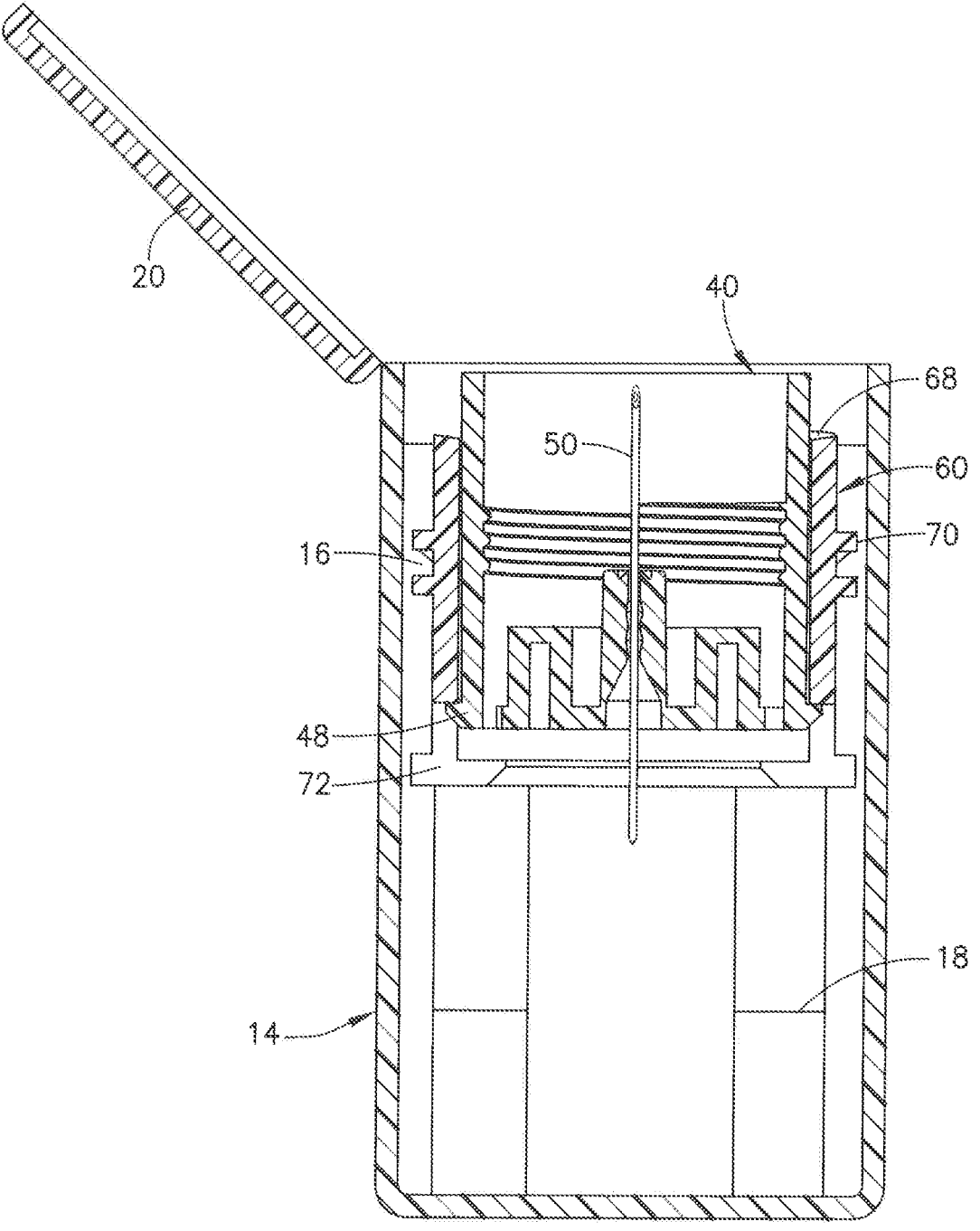
FIG. 16 shows an alternate cross-sectional view of the compartment in the pen needle magazine of FIG. 1 with the used pen needle returned to the first position.

FIGS. 15 and 16 illustrate the pen needle orientate retaining element 70 of the pen needle orientate 60 engaged with the compartment-retaining element 16 of the compartment 14. This engagement keeps the pen needle orientate 60 in the first position. These figures also show the pen needle snap lock 48 of the pen needle 40 engaged to the pen needle orientate snap lock 72 of the pen needle orientate 60 in a locked position. As the pen needle 40 is placed back into the pen needle orientate 60, the follower guide element 46 travels downward in the second pen needle path 64. As the pen needle 40 travels downward in this manner, the pen needle snap lock 48 is compressed inwardly. When the follower guide element 46 reaches the distal end of the second pen needle path 64, the pen needle snap lock 48 expands to its natural shape to engage the pen needle orientate snap lock 72, as illustrated in FIG. 16. In this position, the pen needle 40 is locked axially and rotationally in the pen needle orientate 60.

Figure 17:
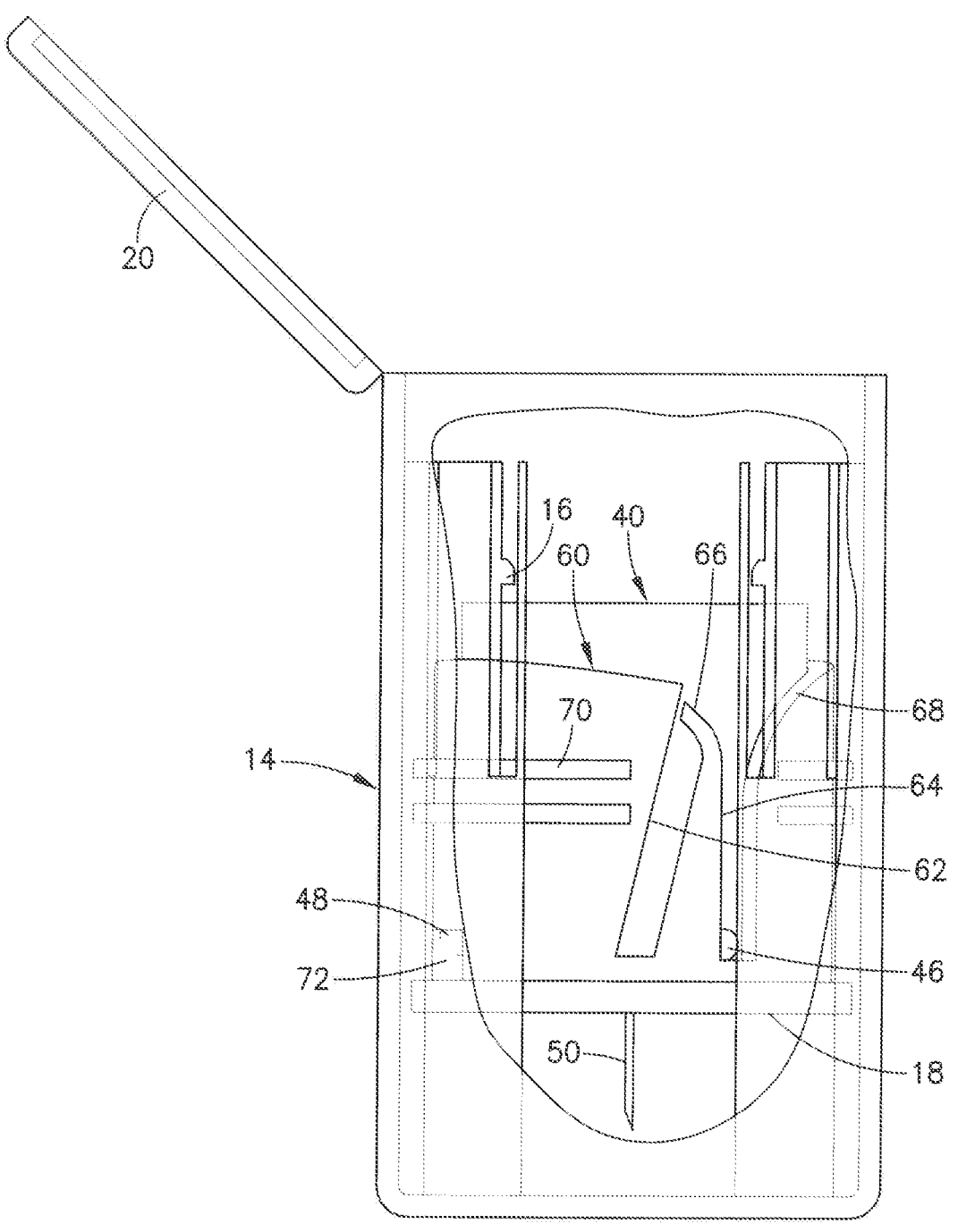
FIG. 17 shows a cross-sectional view of the compartment in the pen needle magazine of FIG. 1 with the pen needle in a second position.

FIG. 17 shows the pen needle 40 and the pen needle orientate 60 in the second position within the compartment 14. After the pen needle 40 is locked to the pen needle orientate 60 as described above, the user applies additional force to the medication delivery pen 2 to move the pen needle 40 downward further into the compartment 14. Specifically, the chamfered top surface of the compartment-retaining element 16 allows for the pen needle orientate retaining element 70 to overcome the engagement in the first position and move downward into the compartment 14 toward the second position. When the pen needle orientate 60 overcomes this engagement, an audible sound or tactile feedback is advantageously provided to indicate such movement. The bottom surface of the compartment-retaining element 16 is a flat surface that prevents the pen needle 40 from moving upwards and exiting the compartment 14.

The pen needle 40 is moved downward to the second position where a distal end of the pen needle orientate 60 contacts the bottom-stepped surface 18 of the compartment 14. In this manner, the distal end of the needle 50 of the pen needle 40 is unaffected and does not make contact with a bottom surface of the compartment 14. The second position also advantageously provides reduced access of the pen needle 40 from the top surface of the compartment 14. This configuration advantageously prevents the non-patient end of the needle 50 of the pen needle 40 from exposure and minimizes needle stick.

The inner shield 80 is not returned to the pen needle 40 after use of the pen needle 40. Instead, the inner shield 80 is discarded prior to using the pen needle 40. Accordingly, the extra space previously taken up by the inner shield 80 provides the necessary space for the pen needle 40 to travel downward to the second position and be inaccessible to the medication delivery pen 2. The second position advantageously acts as a visual indicator to the user indicating that the pen needle 40 can no longer be used. This configuration advantageously prevents reuse of the pen needle 40.

Figure 18:
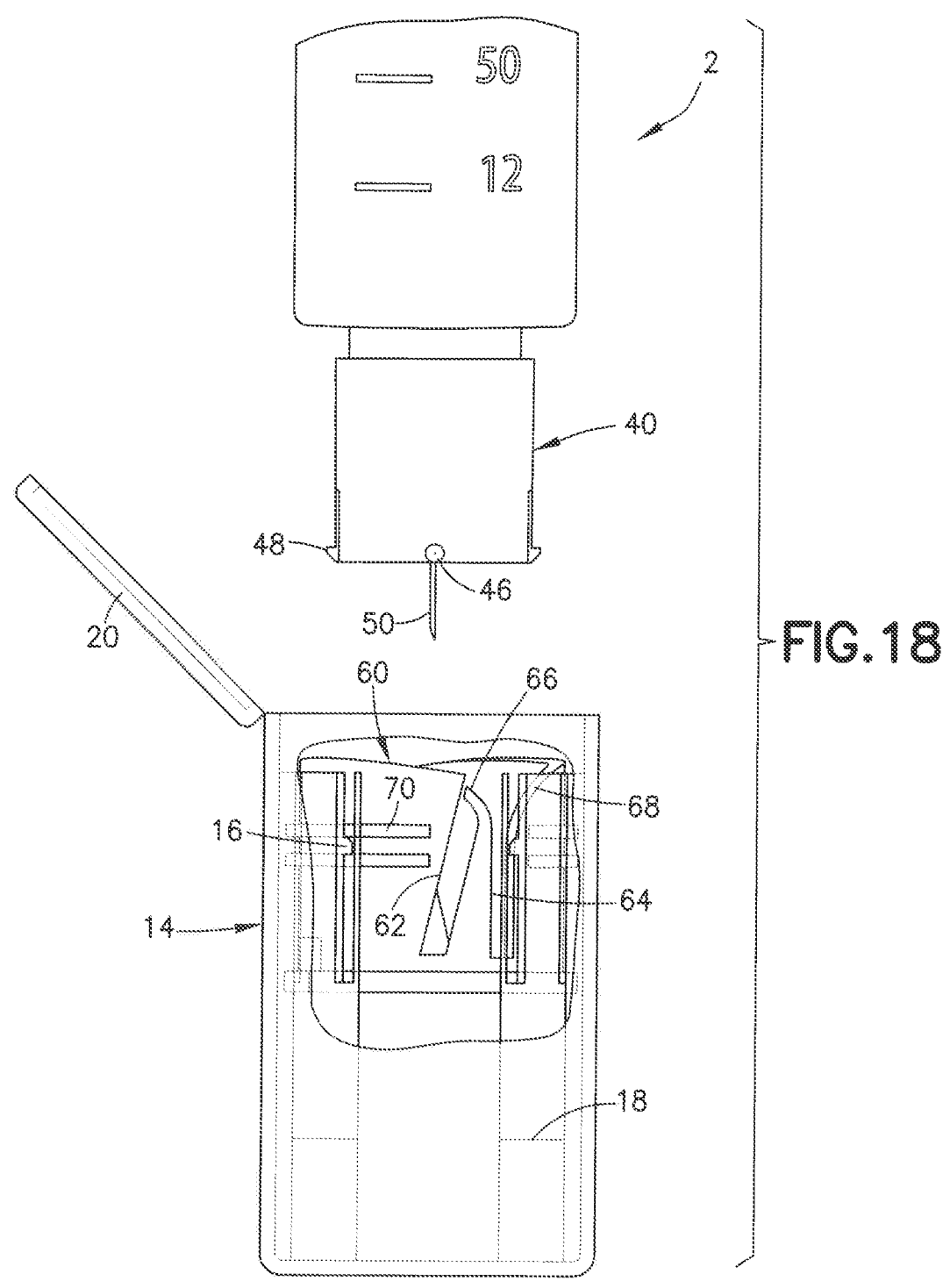
FIG. 18 shows the used pen needle engaged to the medication delivery pen preparing to be disposed in the compartment of FIG. 6.

FIGS. 18-21 show how the used pen needle 40 is discarded into the pen needle magazine 10. FIG. 18 shows the used pen needle 40 engaged to the medication delivery pen 2. The pen needle orientate 60 is in the first position via engagement of the pen needle orientate retaining element 70 and the compartment-retaining element 16 of the compartment 14 as previously described. In addition, the inner shield 80 has been discarded and no longer used.

Figure 19:
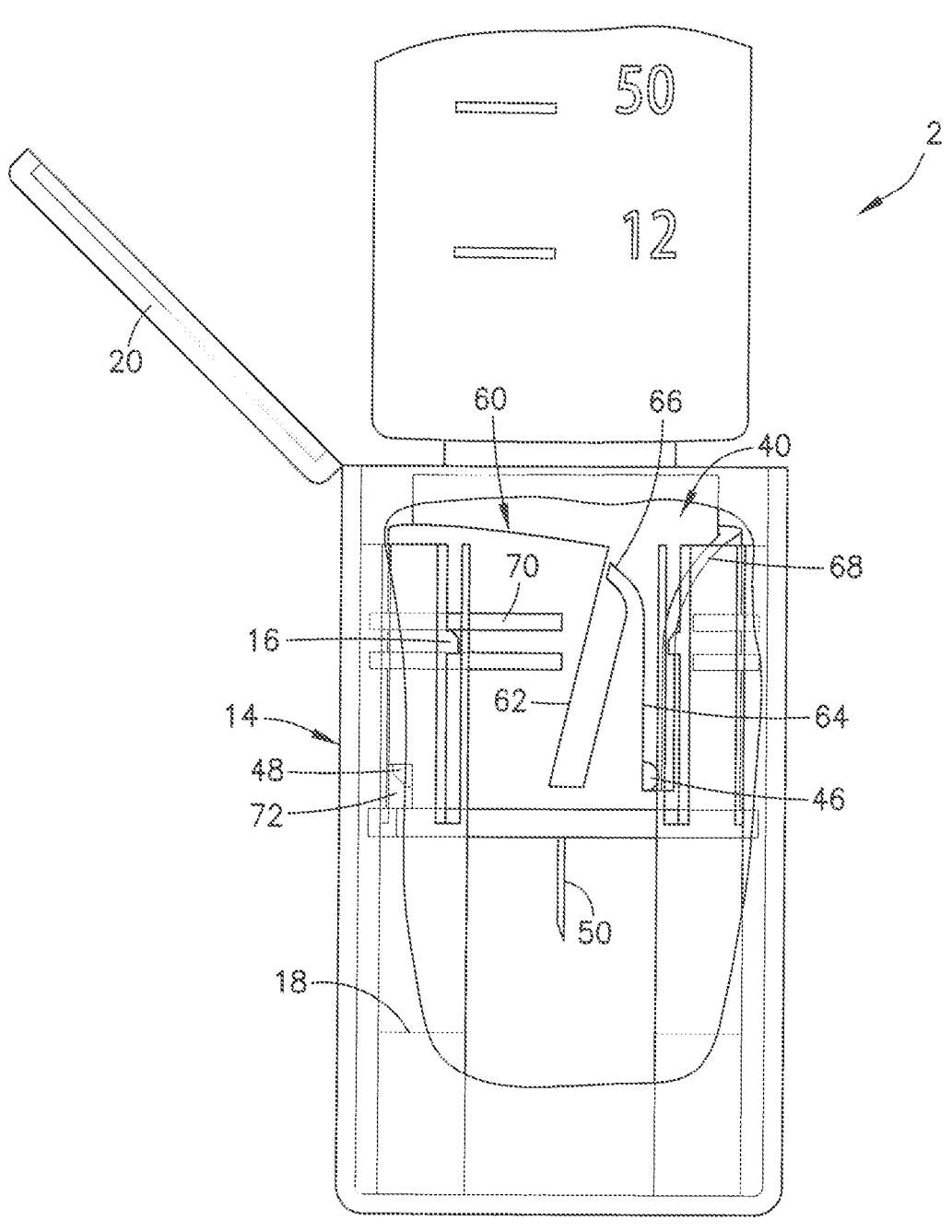
FIG. 19 shows the pen needle engaged to the pen needle orientate in the compartment of FIG. 18 in the first position.

FIG. 19 shows the pen needle 40 disposed in the pen needle orientate 60. Specifically, the follower guide element 46 of the pen needle 40 travels downward into the second pen needle path 64 with the assistance of the pen needle path curvature 68 of the pen needle orientate 60. During this downward movement, the pen needle snap lock 48 is compressed inwardly. When the follower guide element 46 reaches the distal end of the second pen needle path 64, the pen needle snap lock 48 expands outwardly to engage and lock to the pen needle orientate snap lock 72. This is because the pen needle orientate snap lock 72 is advantageously positioned at a predefined angle with respect to the second pen needle path 64.

The follower guide element 46 is not able to travel downward into the first pen needle path 64 because of the path obstruction 66. The path obstruction 66 acts as a one way valve and can only be opened when the follower guide element 46 is in the first pen needle path 62 and the pen needle 40 is removed from the pen needle orientate 60.

FIG. 20 shows the pen needle 40 locked to the pen needle orientate 60 and moving from the first position toward the second position. Specifically, the pen needle orientate retaining element 70 moves past the compartment-retaining element 16 of the compartment 14. A chamfer in the top surface of the compartment-retaining element 16 allows for the pen needle orientate retaining element 70 to move and overcome the engagement. During this movement, an audible sound or a tactile feedback is provided to indicate such movement.

Finally. FIG. 21 illustrates the medication delivery pen 2 disengaged from the pen needle 40. Specifically, the thread 4 of the medication delivery pen 2 is unthreaded from the inner thread 44 of the pen needle 40. In addition, the pen needle 40 is locked to the pen needle orientate 60 and disposed in the second position. Specifically, a bottom surface of the pen needle orientate 60 contacts the bottom-stepped surface 18 of the compartment 14. The pen needle 40 is now advantageously recessed from the top surface of the compartment 14 and inaccessible by the medication delivery pen 2. The compartment door 20 can then be closed to enclose the compartment 14.

After all the pen needles 40 are used and returned to the second position in each of the compartments 14 of the pen needle magazine 10, the user can advantageously send the pen needle magazine 10, via mail, for example, to a manufacturer or a waste management entity for safe and sterile disposal. Optionally, the manufacturer can advantageously recycle and reuse various components of the pen needle magazine 10. For example, the manufacturer can sterilize and reuse some or all of the compartments 14 in the pen needle magazine 10. Specifically, the manufacturer can replace the used pen needle 40 with the unused pen needle 40 in one or more compartments 14 and seal the respective compartment 14 with the seal 30. The pen needle magazine 10 can then be shipped and ultimately sold for reuse.

The storage and use of the pen needles 40, as well as the disposal of the pen needles 40 in the same pen needle magazine 10 provides many advantages and benefits. There is no need for separate packages for storage and disposal of pen needles 40. This is because the pen needle magazine 10 advantageously synchronizes needle attachment and removal with needle detachment and disposal. This versatile arrangement provides better usage, optimizes workflow, minimizes setup time and optimizes space.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. In addition, any of the embodiments, features and/or elements disclosed herein may be combined with one another to form various additional combinations not specifically disclosed, as long as the embodiments, features and/or elements being combined do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. A pen needle magazine, comprising:
a plurality of compartments each carrying a pen needle; and
a pen needle carrier disposed in each of the plurality of compartments, the pen needle disposed in the pen needle carrier; wherein:
the pen needle carrier includes a first pen needle path and a second pen needle path;
the first pen needle path aids in removing the pen needle; and
the second pen needle path aids in discarding a used pen needle.

2. The pen needle magazine of claim 1, wherein the plurality of compartments each includes a retaining element that allows the pen needle carrier to move between a first position and a second position in a corresponding compartment of the plurality of compartments.

3. The pen needle magazine of claim 2, wherein the retaining element prohibits removal of the pen needle carrier from the corresponding compartment.

4. The pen needle magazine of claim 3, wherein the pen needle carrier includes a retaining element that cooperates with the retaining element of the corresponding compartment.

5. The pen needle magazine of claim 1, wherein the pen needle includes a guide element that is configured to travel along one of the first needle path or the second pen needle path.

6. The pen needle magazine of claim 1, wherein the pen needle and the pen needle carrier each include a snap lock that engage when the pen needle is guided along the second pen needle path.

7. The pen needle magazine of claim 6, wherein the snap lock of the pen needle carrier is angularly positioned with respect to the second pen needle path.

8. The pen needle magazine of claim 6, wherein the snap lock of the pen needle and the snap lock of the pen needle carrier engage when the pen needle is at a distal end of the second pen needle path.

9. The pen needle magazine of claim 1, wherein the pen needle carrier includes a path obstruction disposed at a proximal end of the first pen needle path.

10. The pen needle magazine of claim 9, wherein the path obstruction selectively opens to allow a guide element of the pen needle to exit the first pen needle path.

11. The pen needle magazine of claim 9, wherein the path obstruction prevents a guide element of the pen needle to reenter the first pen needle path after exiting.

12. The pen needle magazine of claim 1, wherein the pen needle carrier includes a pen needle path curvature.

13. The pen needle magazine of claim 12, wherein a guide element of the pen needle travels on the pen needle path curvature to enter into the second pen needle path.

14. The pen needle magazine of claim 1, further comprising an inner shield that encloses a needle of the pen needle prior to use.

15. The pen needle magazine of claim 1, further comprising a seal disposed on a top surface of each of the plurality of compartments to enclose a pen needle in a corresponding compartment.

16. The pen needle magazine of claim 15, further comprising a plurality of compartment doors that each cover the corresponding compartment.

17. The pen needle magazine of claim 15, wherein each seal is disposed between the top surface of one of the plurality of compartments and a corresponding compartment door.

18. The pen needle magazine of claim 15, wherein:

the seal includes a sealing portion and a tab portion;

the sealing portion is disposed between the top surface of one of the plurality of compartments and a corresponding compartment door; and the tab portion is disposed adjacent to the corresponding compartment door.

19. A pen needle magazine, comprising:

a plurality of compartments each carrying a pen needle;

a pen needle carrier disposed in each of the plurality of compartments, the pen needle disposed in the pen needle carrier, wherein:

the pen needle carrier includes a first pen needle path and a second pen needle path;

the first pen needle path aids in removing the pen needle; and the second pen needle path aids in discarding a used pen needle;

a seal disposed on a top surface of each of the plurality of compartments to enclose a pen needle in a corresponding compartment; and a plurality of compartment doors that each cover a corresponding compartment, wherein the seal is disposed between the top surface of one of the plurality of compartments and a corresponding compartment door.

20. A pen needle magazine, comprising:

a plurality of compartments each carrying a pen needle;

a pen needle carrier disposed in each of the plurality of compartments, the pen needle disposed in the pen needle carrier, wherein:

the pen needle carrier includes a first pen needle path and a second pen needle path;

the first pen needle path aids in removing the pen needle; and the second pen needle path aids in discarding a used pen needle;

a seal disposed on a top surface of each of the plurality of compartments to enclose a pen needle in a corresponding compartment; and a plurality of compartment doors that each cover a corresponding compartment, wherein:

the seal includes a sealing portion and a tab portion;

the sealing portion is disposed between the top surface of one of the plurality of compartments and a corresponding compartment door; and the tab portion is disposed adjacent to the corresponding compartment door.

* * * * *